(12) United States Patent
Horst

(10) Patent No.: US 7,389,676 B2
(45) Date of Patent: Jun. 24, 2008

(54) EGG TESTING APPARATUS AND METHOD

(76) Inventor: Patricia J. Horst, 1802 Birchwood La., Rockford, IL (US) 61107

( * ) Notice: Subject to any disclaimer, the term of this patent is extended or adjusted under 35 U.S.C. 154(b) by 0 days.

(21) Appl. No.: 11/286,776

(22) Filed: Nov. 22, 2005

(65) Prior Publication Data

US 2006/0174694 A1 Aug. 10, 2006

Related U.S. Application Data

(60) Provisional application No. 60/650,244, filed on Feb. 4, 2005.

(51) Int. Cl.
*G01N 9/00* (2006.01)
*G01N 9/32* (2006.01)
(52) U.S. Cl. .................... 73/32 R; 73/866; 426/231
(58) Field of Classification Search ............ 73/32 R
See application file for complete search history.

(56) References Cited

U.S. PATENT DOCUMENTS

| | | | | |
|---|---|---|---|---|
| 1,516,738 A | * | 11/1924 | Kasser | 209/173 |
| 1,712,736 A | * | 5/1929 | Nichols | 346/33 D |
| 1,760,658 A | * | 5/1930 | Pampe | 73/32 R |
| 2,037,899 A | * | 4/1936 | Harrison | 73/437 |
| 2,209,077 A | * | 7/1940 | Gandrud | 73/32 R |
| 5,275,818 A | * | 1/1994 | Kind | 434/157 |
| 6,652,005 B2 | * | 11/2003 | Meischen | 283/81 |

OTHER PUBLICATIONS

Matthews, Scott, How to Tell a Bad Egg, http:www.backwoodshome.com/articles/matthews53.html, 1998.*
Why Do Some Eggs Float?-Fresh Eggs vs. Old Eggs, http://whatcookingamerica.net/Eggs/EggsFloat.htm, undated.*
Search Results for "Egg" at Backwoods Home Magazine: http://www.backwoodshome.com/cgibin/ksearch/ksearch.cgi?terms=egg&x=22&y=16.*
Previous Issues of Backwoods Home Magazine: http://www.backwoodshome.com/previssue.html, pp. 1-4.*
"Internet Archive Wayback Machine" Searched for http://www.backwoodshome.com/articles/matthews53.html, published Nov. 19, 2000. Accessed Mar. 9, 2007.*
"How to tell if you've got a bad egg", author unknown http://web.archive.org/web/20021224055412/http://www.ochef.com/789.htm, Dec. 24, 2002 Accessed Mar. 9, 2007.*
"How can we tell the age of an egg in water", Katrin Becker http://www.minkhollow.ca./HatchingProgram/Candling/LearnMore/EggWater.html, 2004 Accessed Jun. 19, 2007.*
"How to Tell if an Egg is Fresh", author unknown, Omlet UK http://www.omlet.co.uk/guide/guide.php?view=Chickens&cat=Eggs&sub=freshness, 2004 Accessed Jun. 19, 2007.*
"How to tell a bad egg", Scott Mathews http://web.archive.org/web/20001119082200/http://www.backwoodshome.com/articles/matthews53.html, Nov. 19, 2000 Accessed Mar. 9, 2007.*
"Why Do Some Eggs Float?", author unknown http://whatscookingamerica.net/Eggs/EggsFloat.htm, date unknown Accessed May 25, 2006.*
"Eggsperiments' Activity Sheet", Science on the Shelves, Dept. of Chemistry, University of York, UK Mar. 2003.*

* cited by examiner

*Primary Examiner*—Hezron E. Williams
*Assistant Examiner*—Samir M. Shah
(74) *Attorney, Agent, or Firm*—Reinhart Boerner Van Deuren P.C.

(57) ABSTRACT

An egg testing apparatus and method utilize a vessel having marked thereupon indicia including graphics, calibrations and text, for use in determining the freshness, approximate age and recommended use for a chicken egg immersed inside the vessel in a volume of cool, fresh (i.e. non-salted) water.

10 Claims, 5 Drawing Sheets

EGG TESTING APPARATUS AND METHOD

CROSS-REFERENCE TO RELATED PATENT APPLICATIONS

This patent application claims the benefit of U.S. Provisional Patent Application No. 60/650,244, filed Feb. 4, 2005, the disclosure and teachings of which are incorporated herein, in their entirety, by reference.

FIELD OF THE INVENTION

This invention relates to testing chicken eggs, and more particularly to determining the freshness of chicken eggs and their suitability for human consumption.

BACKGROUND OF THE INVENTION

It is desirable to have a convenient method and apparatus for testing chicken eggs to determine their freshness and suitability for human consumption. More particularly, it is desirable to have such a method and apparatus that can be conveniently used in a typical household kitchen.

Unfertilized chicken eggs have a typical useful life of about 31 days, if they are transported and stored in an appropriate environment. Many factors, including storage temperature and humidity, will affect the length of time that eggs can be maintained in a condition suitable for human consumption.

For eggs purchased from reliable grocers, date codes on the egg cartons can be relied upon to some extent for determining how old and fresh the eggs in the carton are likely to be, but this method is not infallible due to the many factors which can influence freshness and shelf life as the eggs make their way from the henhouse to the refrigerator shelf. Eggs from Free-Range chickens are particularly troublesome in this regard, because the eggs may not be gathered as quickly as commercial laying house eggs, given that the chickens may lay them in a place where they will not be immediately discovered.

It is known that as eggs age, they lose moisture through the shell, and a small air pocket inside the shell gets larger. It is also known that the freshness of a chicken egg may be tested by placing the egg in a vessel containing cool fresh water, and observing whether the egg floats, completely or partially in the water.

Specifically, it is known that a fresh egg will lie on its side on the bottom of the vessel. A slightly older egg will still lie generally on the bottom, but the larger end of the egg may float slightly off the bottom. As the egg continues to age, it will stand in the water with its small end touching the bottom. At a few more days of age, the egg will begin to bob up off of the bottom and float part way up in the water. A really old egg will float high in the water, perhaps even on the surface of the water.

For direct consumption, eggs which lie on the bottom are the freshest and most desirable. Eggs which are somewhat less fresh may still be quite good for direct consumption. Eggs which are less fresh yet may still be used for baking and in other indirectly consumed food products. Floating eggs should not be used for human consumption.

Although the above stated information regarding testing of eggs for freshness in water has been known for many years, the method is imprecise and prone to mistakes in interpretation. What is needed is an improved method and apparatus for more precisely determining the freshness of chicken eggs and their suitability for human consumption, in a manner that can be utilized in a typical household kitchen

BRIEF SUMMARY OF THE INVENTION

The invention provides a calibrated vessel for testing a parameter related to the freshness of chicken eggs, by filling the vessel to a marked level with cool fresh water and observing the manner in which an egg immersed in the water sinks or floats in relation to indicia on the vessel. In some forms of the invention, the indicia includes graphical representations showing outlines of eggs in various attitudes and at various levels in the vessel, together with graphics or text illustrating the freshness and/or best use for the egg. The graphics and/or text may also include calibrations indicating the approximate age of the egg. In some forms of the invention, only calibrations may be given, and in others only graphics may be provided on the vessel. The vessel may also bear instructions for use in testing eggs, and additional indicia for use as a standard measuring vessel for liquid or dry volume.

Other aspects, objectives and advantages of the invention will be apparent from the following description of the invention, in conjunction with the accompanying drawings.

BRIEF DESCRIPTION OF THE DRAWINGS AND ATTACHMENTS

While the invention will be described in connection with certain preferred embodiments, there is no intent to limit it to those embodiments. On the contrary, the intent is to cover all alternatives, modifications and equivalents as included within the spirit and scope of the invention.

DESCRIPTION OF THE INVENTION

Figure 1:
FIGS. 1 and 2 show a first exemplary embodiment of an egg tester, according to the invention, in the form of a vessel bearing indicia including calibrations and text.
Figure 2:
Figure 3:
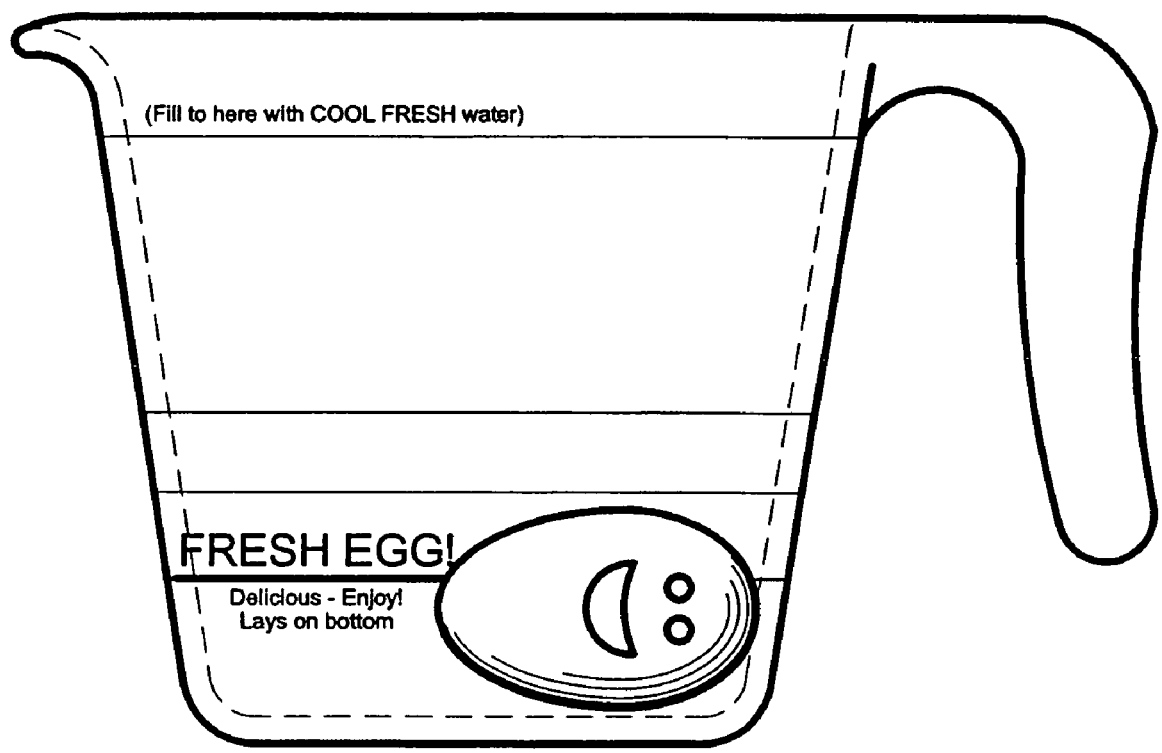
FIGS. 3-5 show a second exemplary embodiment of an egg tester, according to the invention, in the form of a vessel bearing indicia including calibrations, text, graphics and instructions for use.
Figure 4:
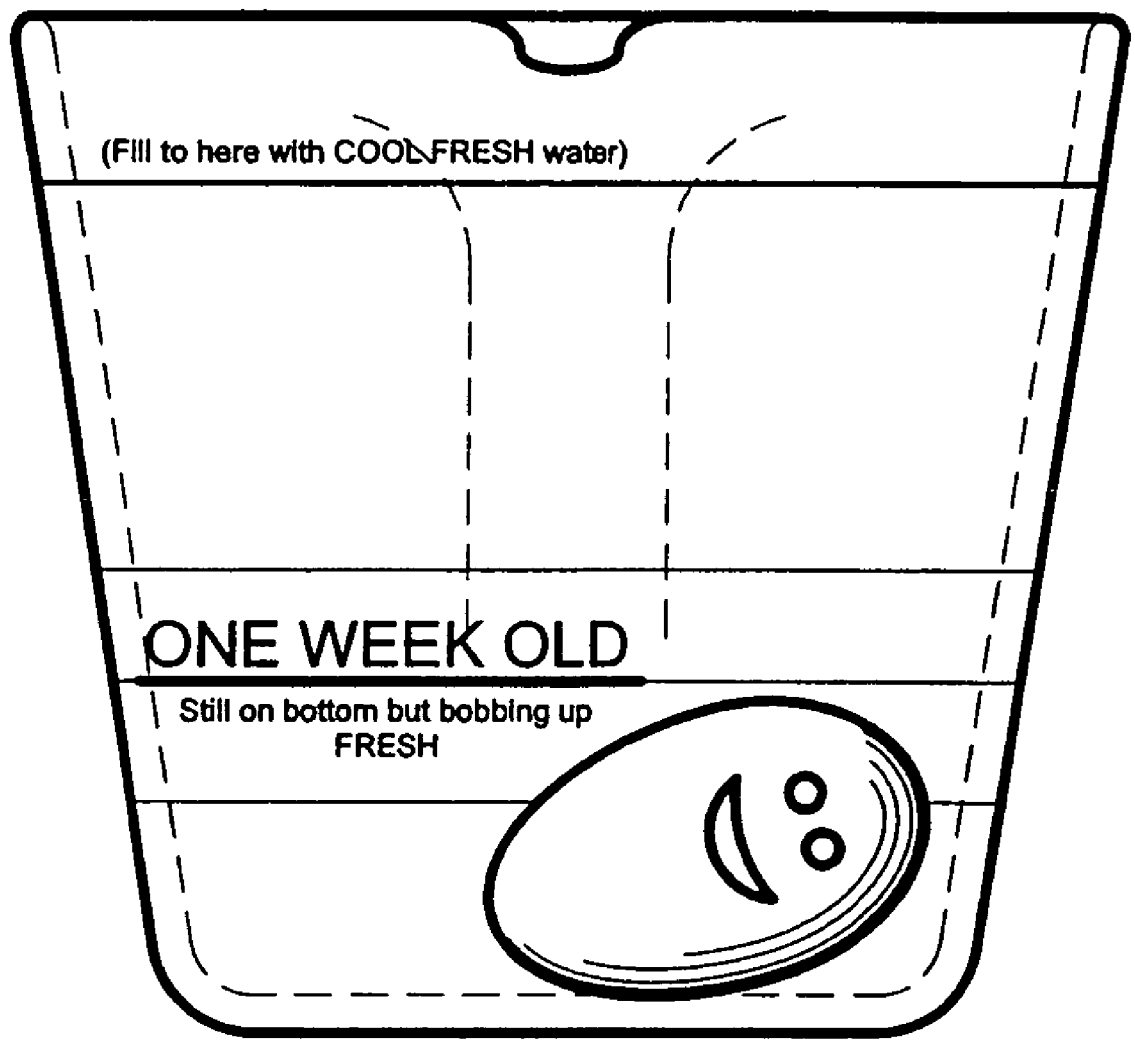
Figure 5:
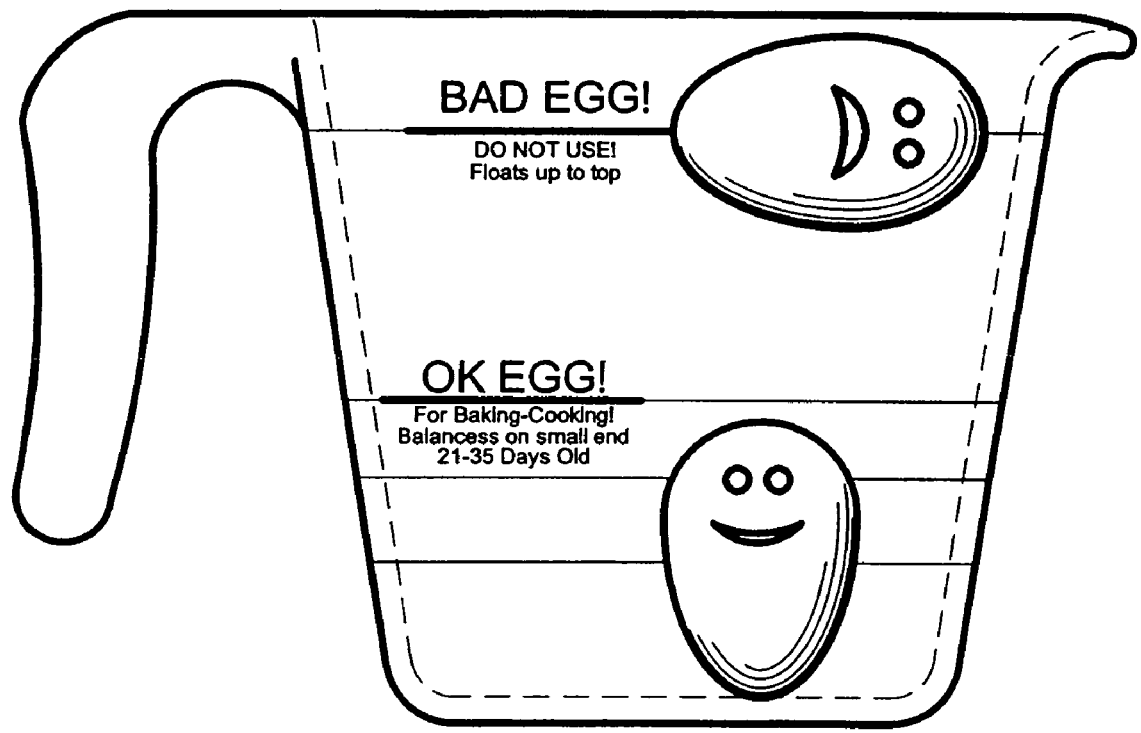

FIGS. 1-5 show exemplary embodiments of an egg testing apparatus, according to the invention, in the form of a vessel having marked thereon indicia including graphics, calibrations and text, for use in determining parameters such as the freshness, approximate age and recommended use for an egg immersed inside the vessel in a volume of cool, fresh (i.e. non-salted) water. Specifically, FIGS. 1 and 2 show a first exemplary embodiment of an egg tester, according to the invention, in the form of a vessel bearing indicia including calibrations and text. FIGS. 3-5 show a second exemplary embodiment of an egg tester, according to the invention, in the form of a vessel bearing indicia including calibrations, text, graphics and instructions for use. Those having skill in the art will recognize that in other forms of the invention, the vessel, graphics, calibrations and text may take many other forms.

It is preferred that the vessel have walls that are at least partially transparent so that the egg can be viewed through the walls and compared to the indicia on the vessel, but vessels that are translucent or opaque can also be used in practicing the invention. The indicia may be placed on the outside of the walls, the inside of the walls, within the walls or any combination of these locations.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any element not expressly described herein as being essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited or suggested herein as permitted by applicable law. Moreover, any combination of the above-described elements in all possible variations thereof is encompassed by the invention unless otherwise indicated herein or otherwise clearly contradicted by context.

What is claimed is:

1. An apparatus for testing a chicken egg, the apparatus comprising:
    a vessel for receiving a volume of cool fresh water sufficient to fill the vessel to a depth allowing the egg being tested to float within the volume of water, should the buoyancy of the egg being tested be such that the egg being tested would float partially or fully in the water; and
    indicia marked upon the vessel for determining a parameter related to the freshness of the chicken egg being tested, when the egg being tested is placed unconstrained in the volume of water, in a random orientation within the vessel, through comparison of the position and attitude assumed by the chicken egg being tested in the volume of water, with respect to the indicia;
    the vessel defining a bottom inside surface thereof;
    the indicia on the vessel including a plurality of graphical representations of an egg in a plurality of alternative positions and attitudes, with some of the plurality of graphical representations showing the egg in contact with the bottom inside surface of the vessel, some of the graphical representations showing the egg standing on one end at various angles with the one end still in substantial contact with the bottom inside surface of the vessel, and with some of the graphical illustrations showing the egg floating out of contact with the bottom inside surface within the vessel;
    the graphical representations being such that comparison of the graphical representations to the assumed position and attitude of the egg being tested may be made without having the egg being tested positioned in any particular orientation or location within the vessel.

2. The apparatus of claim 1, wherein, the indicia includes calibrations indicative of the approximate age of the egg being tested.

3. The apparatus of claim 2, wherein, the indicia includes text describing the freshness of the egg being tested, in consideration of the nearest match between the attitude and position of the egg being tested as compared to the indicia on the vessel.

4. The apparatus of claim 2, wherein, the indicia includes text describing the best use of the egg being tested, in consideration of the nearest match between the attitude and position of the egg being tested as compared to the indicia on the vessel.

5. The apparatus of claim 1, wherein, the indicia includes text describing the freshness of the egg being tested, in consideration of the nearest match between the attitude and position of the egg being tested as compared to the indicia on the vessel.

6. A method for testing a chicken egg, the method comprising:
    filling a vessel in accordance with claim 1 with a volume of water to a depth of the water within the vessel sufficient for allowing the egg being tested to float within the volume of water;
    placing the egg to be tested into the volume of the water, without regard to the position or orientation of the egg within the vessel, and without constraining the egg fully or partially in contact with the vessel;
    allowing the egg being tested to assume an orientation and position within the volume of water in the vessel; and
    comparing a position and attitude of the chicken egg being tested in the volume of water to the indicia marked upon the vessel.

7. The method of claim 6, wherein, the indicia includes calibrations indicative of an approximate age of the egg being tested, and the method further comprises determining the approximate age of the egg from the calibrations.

8. The method of claim 6, wherein, the indicia includes text describing the freshness of the egg being tested, in consideration of the nearest match between the attitude and position of the egg being tested as compared to the indicia on the vessel, and the method further comprises determining the freshness of the egg being tested as indicated by the test.

9. The method of claim 6, wherein, the indicia includes text describing the best use of the egg being tested, in consideration of the nearest match between the attitude and position of the egg being tested as compared to the indicia on the vessel, and the method further comprises determining the best use of the egg being tested as indicated by the test.

10. The apparatus of claim 1, wherein, the indicia includes text describing the best use of the egg being tested, in consideration of the nearest match between the attitude and position of the egg being tested as compared to the indicia on the vessel.

* * * * *